(12) United States Patent
Hewitt et al.

(10) Patent No.: US 7,882,836 B2
(45) Date of Patent: Feb. 8, 2011

(54) DIAPHRAGM VALVE FOR A RESPIRATOR

(75) Inventors: Brian Hewitt, Grossbritannien (GB); Piers Antony James, Grossbritannien (GB)

(73) Assignee: Dräger Medical GmbH, Lübeck (DE)

( * ) Notice: Subject to any disclaimer, the term of this patent is extended or adjusted under 35 U.S.C. 154(b) by 1569 days.

(21) Appl. No.: 11/210,167

(22) Filed: Aug. 23, 2005

(65) Prior Publication Data
US 2006/0076016 A1  Apr. 13, 2006

(30) Foreign Application Priority Data
Oct. 7, 2004  (DE) .................... 10 2004 049 151

(51) Int. Cl.
*A61M 16/00* (2006.01)
*A62B 9/02* (2006.01)
*G05D 7/00* (2006.01)
*F16K 15/00* (2006.01)
*F16K 31/44* (2006.01)
*F16K 25/00* (2006.01)
*F16K 1/48* (2006.01)
*B22D 41/16* (2006.01)

(52) U.S. Cl. .............. 128/205.24; 128/203.11; 128/205.13; 137/102; 137/512.2; 137/512.4; 251/77; 251/78; 251/84; 251/86; 251/356; 251/257

(58) Field of Classification Search ............ 128/203.11, 128/205.13, 205.24; 137/102, 512.2, 512.4; 251/77, 78, 84, 86, 356, 357
See application file for complete search history.

(56) References Cited

U.S. PATENT DOCUMENTS
5,103,854 A * 4/1992 Bailey et al. ................. 137/102

FOREIGN PATENT DOCUMENTS
DE           33 41 711 C2     5/1985

* cited by examiner

*Primary Examiner*—Patricia M Bianco
*Assistant Examiner*—Nihir Patel
(74) *Attorney, Agent, or Firm*—McGlew and Tuttle, P.C.

(57) ABSTRACT

A diaphragm valve is provided, in which there is improved sealing of a closing cover (15) against the valve housing (3). The seal includes a cylindrical sealing washer (25), which is connected to the valve housing (3) in one piece and into which a cylindrical wall section (18) of the closing cover (15) can be inserted with press fit.

13 Claims, 2 Drawing Sheets

DIAPHRAGM VALVE FOR A RESPIRATOR

CROSS REFERENCE TO RELATED APPLICATIONS

This application claims the benefit of priority under 35 U.S.C. §119 of German Application DE 10 2004 049 151.8 filed Oct. 7, 2004, the entire contents of which are incorporated herein by reference.

FIELD OF THE INVENTION

The present invention pertains to a controllable diaphragm valve for a respirator/ventilator.

BACKGROUND OF THE INVENTION

A diaphragm valve of the type mentioned, i.e., for a respirator/ventilator (breathing equipment), has become known from DE 33 41 711 C2. A valve chamber and a control chamber, which are separated from one another by means of a diaphragm, are located in a valve housing with a gas feed line and a gas outlet line. The gas feed line leads to a valve seat, which is closed by the diaphragm or is released depending on the pressure in the control chamber. The valve housing has an essentially cylindrical design, and a closing cover, which is sealed against the valve housing by means of an O-ring, is located at the end of the control chamber.

The drawback of the prior-art diaphragm valve is that a separate sealing ring, which makes assembly difficult, is needed to seal the closing cover against the valve housing.

SUMMARY OF THE INVENTION

The basic object of the present invention is to provide a diaphragm valve that has a better sealing of the closing cover against or relative to the valve housing.

According to the invention, a diaphragm valve for a respirator is provided with a gas feed line, which leads in a valve housing into a valve chamber and ends in a valve seat. A gas outlet line leads out of the valve chamber. A valve body spans over the valve chamber. With the valve body the valve seat can be closed and the flow of gas from the gas feed line into the gas outlet line can be interrupted. With the valve body a control chamber is formed within the valve housing, separated from the valve chamber. A closing cover closes a cylindrical control chamber end of the valve housing. A cylindrical, flexible sealing washer is connected with the valve housing in one piece. The cylindrical, flexible sealing washer is provided at the control chamber end. A cylindrical wall section of the closing cover is designed as a wall section that can be inserted into the sealing washer with a press fit.

The advantage of the diaphragm valve according to the present invention is essentially that a cylindrical circumferential joint, which is connected with the valve housing in one piece, and into which a cylindrical wall section of the closing cover is inserted with press fit, is provided at the outwardly directed end of the control chamber. Both the valve housing and the circumferential joint consist of an elastomer material, so that the circumferential joint can be injection molded directly on the valve housing. The wall thickness of the circumferential joint is selected to be such that it is slightly stretched during the insertion of the closing cover and is sealingly in contact with the cylindrical wall section of the closing cover as a result.

The closing cover is advantageously fastened to the valve housing by means of a snap-in connection. Locking cams located on the inside are provided for this purpose at a cover mount of the valve housing, and a locking ring, which slides over the locking cams when the closing cover is inserted into the valve housing and then snaps in, is located at the end of the closing cover. At the same time, the cylindrical wall section of the closing cover engages the circumferential joint.

The length of the circumferential joint is advantageously in a range of 2.5 mm to 3.5 mm, the wall thickness is 0.8 mm to 1.2 mm, and the internal diameter of the circumferential joint has a value between 43 mm and 45 mm. Preferred dimensions are a length of 3 mm, a wall thickness of 1.2 mm and an internal diameter of 44 mm.

A lead-in bevel for the closing cover with an opening angle of 120° or an angle of 60° in relation to the horizontal is provided at the front end of the circumferential joint. Damage to the circumferential joint during the insertion of the closing cover is prevented from occurring by the lead-in bevel.

The valve housing consists of polypropylene and the closing cover of polyethylene. This material combination of the valve housing and the closing cover has proved to be particularly advantageous, because polyethylene is somewhat softer than polypropylene and the closing cover can therefore adapt well to the circumferential joint.

An exemplary embodiment of the present invention is shown in the figure and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
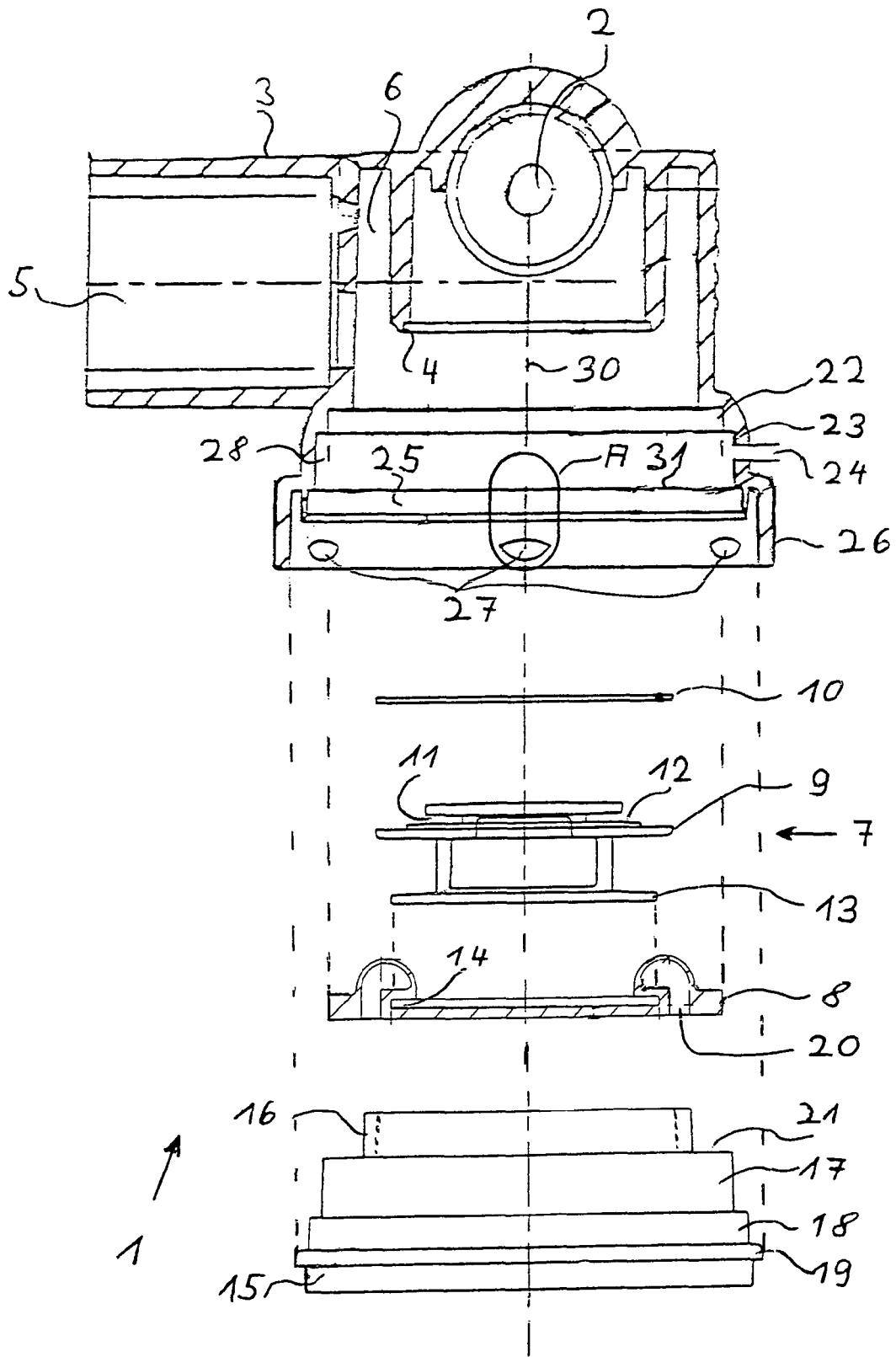
FIG. 1 is an exploded view of the diaphragm valve according to the present invention.

Referring to the drawings in particular, FIG. 1 illustrates the diaphragm valve 1 according to the present invention in an exploded view. A gas feed line 2 at a valve housing 3 extends over a valve seat 4 to a gas outlet line 5. As a result, a valve chamber 6 is formed within the valve housing 3. A valve body 7 of the diaphragm valve 1 comprises a diaphragm element 8, a valve support 9 and a sealing washer 10. The sealing washer 10 is buttoned into a groove 11 of the valve support 9 and lies flush on a sealing surface 12. A disk-shaped fastening element 13 at the valve support 9 is held in a recess 14 of the diaphragm element 8. A closing cover 15 for the valve housing 3 is of a cylindrical design and has a ring mount 16 for the diaphragm element 8, a control chamber section 17, a cylindrical wall section 18, and a locking ring 19.

The diaphragm element 8 has an annular gap 20, so that the ring mount 16 can be pushed into the gap 20 and the underside of the diaphragm element 8 lies flush on the shoulder 21 of the closing cover.

A diaphragm support 22, a control chamber wall 23 with a control pressure connection 24, a circumferential joint 25, and a cover mount 26 with a locking cam 27 are provided in the valve housing 3 in the area of the diaphragm element 8. The cover mount 26 adjoins the control chamber wall 23, and the circumferential joint 25 is injection molded directly on the end 31 of the control chamber wall 23.

With the closing cover 15 inserted into the valve housing 3, the diaphragm element 8 is located within the diaphragm support 22. The control chamber section 17 and the control chamber wall 23 of the valve housing 3 together form an annular gap, which is the control chamber 28 for the diaphragm element 8. The control pressure, by which the valve support 9 with the sealing washer 10 is pressed against the valve seat 4, is admitted into the control chamber 28 via the control pressure connection 24. The valve chamber 6 is separated by the valve body 7 with the diaphragm element 8 from the control chamber 28.

Before the closing cover 15 is inserted into the valve housing 3, the valve body 7 is first placed on the ring mount 16, so that the valve body 7 is fixed against the closing cover 15. Then, the locking ring 19 will first touch the underside of the locking cams 27. Pressure exerted on the rear side of the closing cover 15 causes the cover mount 26 to expand somewhat, and the locking ring 19 slides over the locking cams 27 and then snaps in. The cylindrical wall section 18 is in contact with the sealing washer 25 in the locked state of the closing cover 15, so that the control chamber 28 is sealed against the environment. The closing cover 15 can be removed from the cover mount 26 only by destroying it, so that reuse of the diaphragm valve 1 after disassembly is no longer possible. The diaphragm valve 1 according to the present invention is preferably used as a disposable article.

Figure 2:
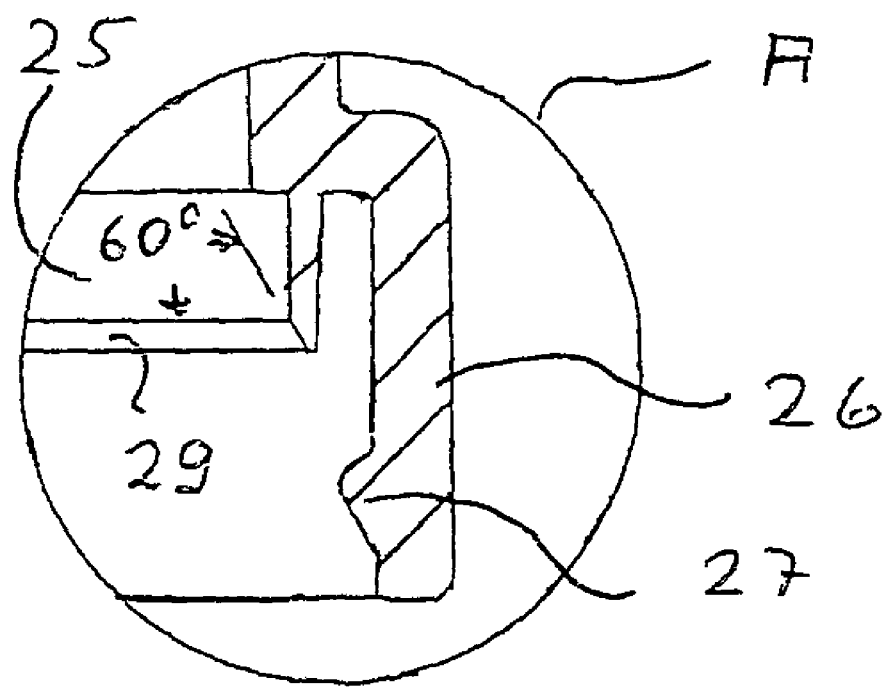
FIG. 2 is a longitudinal sectional view through detail A according to FIG. 1.

FIG. 2 illustrates the detail A according to FIG. 1 in a longitudinal section along the axis of symmetry 30. Identical components are designated by the same reference numbers as in FIG. 1.

At the front end, the circumferential joint 25 has a lead-in bevel 29, which forms an angle of 60° with the horizontal. Damage to the circumferential joint 25 during the insertion of the wall section 18, FIG. 1, is prevented by the lead-in bevel 29 from occurring.

While specific embodiments of the invention have been shown and described in detail to illustrate the application of the principles of the invention, it will be understood that the invention may be embodied otherwise without departing from such principles.

What is claimed is:

1. A diaphragm valve for a respirator, the diaphragm valve comprising:
   a valve housing with a valve chamber ending in a valve seat;
   a gas feed line leading in said valve housing;
   a gas outlet line leading out of said valve chamber;
   a valve body spanning over said valve chamber and disposed to close said valve seat and interrupting the flow of gas from the gas feed line into the gas outlet line, said valve body forming a control chamber within said valve housing, separated from said valve chamber;
   a closing cover closing a cylindrical control chamber end of said valve housing, said closing cover having a cylindrical wall section; and
   a cylindrical, flexible sealing washer connected with said valve housing in one piece, said cylindrical, flexible sealing washer being provided at a control chamber end of said valve housing, said cylindrical wall section of said closing cover having a wall section portion inserted into said sealing washer with a press fit, wherein a snap-in connection fixing said closing cover is present between said closing cover and said valve housing, said snap-in connection comprising a bead-like locking cam at the valve housing and a locking ring at the closing cover, said locking ring being held by said locking cam.

2. A diaphragm valve in accordance with claim 1, wherein said sealing washer has a length of 2.5 mm to 3.5 mm and a wall thickness of 0.8 mm to 1.2 mm.

3. A diaphragm valve in accordance with claim 1, wherein said sealing washer has a lead-in bevel at an entry end of said sealing washer.

4. A diaphragm valve in accordance with claim 3, wherein said lead-in bevel has an angle of the 60° relative to horizontal.

5. A diaphragm valve in accordance with claim 1, wherein said sealing washer has an internal diameter between 43 mm and 45 mm.

6. A diaphragm valve in accordance with claim 1, wherein said valve housing consists of polypropylene and the closing cover consists of polyethylene.

7. A diaphragm valve for a respirator, the diaphragm valve comprising:
   a valve housing with a valve chamber having a valve seat;
   a gas feed line leading in said valve housing;
   a gas outlet line leading out of said valve chamber;
   a valve body disposed to close said valve seat and interrupt the flow of gas from the gas feed line into the gas outlet line, said valve body and at least a portion of said valve housing defining a control chamber within said valve housing, separated from said valve chamber;
   a closing cover closing a cylindrical control chamber end of said valve housing, said closing cover having a cylindrical wall section;
   a sealing washer connected with said valve housing in one piece, said sealing washer being provided at a control chamber end of said valve housing, said cylindrical wall section of said closing cover being inserted into said sealing washer and held in place thereat; and
   a snap-in connection fixing said closing cover at said sealing washer, said snap-in connection comprising a bead-like locking cam at the valve housing and a locking ring at the closing cover, said locking ring being held by said locking cam.

8. A diaphragm valve in accordance with claim 7, wherein said sealing washer has a length of 2.5 mm to 3.5 mm and a wall thickness of 0.8 mm to 1.2 mm.

9. A diaphragm valve in accordance with claim 7, wherein said sealing washer has a lead-in bevel at an entry end of said sealing washer.

10. A diaphragm valve in accordance with claim 9, wherein said lead-in bevel has an angle of the 60° relative to horizontal.

11. A diaphragm valve in accordance with claim 7, wherein said sealing washer has an internal diameter between 43 mm and 45 mm.

12. A diaphragm valve in accordance with claim 7, wherein said valve housing consists of polypropylene and the closing cover consists of polyethylene.

13. A process for forming a diaphragm valve for a respirator, the process comprising:
   providing a valve housing with a valve chamber ending in a valve seat, a gas feed line leading in said valve housing, a gas outlet line leading out of said valve chamber;
   forming the provided valve housing in one piece with a cylindrical flexible sealing washer at a control chamber end of said valve housing;
   positioning a valve body spanning over said valve chamber and disposed to close said valve seat and interrupt the flow of gas from the gas feed line into the gas outlet line, said valve body forming a control chamber within said valve housing, separated from said valve chamber;

providing a closing cover closing a cylindrical control chamber end of said valve housing, said closing cover having a cylindrical wall section; and inserting said cylindrical wall section of said closing cover into said sealing washer and retaining said cylindrical wall section in contact with an inner surface of said sealing washer, said cylindrical wall section being retained in contact with the inner surface of said sealing washer with a press fit of said cylindrical wall section with the inner surface, said press fit being facilitated by a snap-in connection retaining said cylindrical wall section in position relative to said sealing washer, said snap-in connection comprising a bead-like locking cam at the valve housing and a locking ring at the closing cover, said locking ring being held by said locking cam.

* * * * *